(12) United States Patent
Kiuchi et al.

(10) Patent No.: US 8,722,372 B2
(45) Date of Patent: May 13, 2014

(54) METHOD FOR RECOVERING AND PRODUCING ETHANOL AND OIL

(75) Inventors: Takafumi Kiuchi, Kitakyushu (JP); Yasuhiko Kato, Kitakyushu (JP); Yasufumi Hajima, Kitakyushu (JP); Norio Yoshitake, Kitakyushu (JP); Shigeru Mitarai, Kitakyushu (JP)

(73) Assignees: Nippon Steel Engineering Co., Ltd., Tokyo (JP); Nittetsu Plant Designing Corporation, Fukuoka (JP)

( * ) Notice: Subject to any disclaimer, the term of this patent is extended or adjusted under 35 U.S.C. 154(b) by 0 days.

(21) Appl. No.: 13/138,223

(22) PCT Filed: Jan. 22, 2009

(86) PCT No.: PCT/JP2009/050915
§ 371 (c)(1), (2), (4) Date: Oct. 25, 2011

(87) PCT Pub. No.: WO2010/084589
PCT Pub. Date: Jul. 29, 2010

(65) Prior Publication Data
US 2012/0034667 A1 Feb. 9, 2012

(51) Int. Cl.
*C12P 7/06* (2006.01)

(52) U.S. Cl.
USPC .......................................... 435/161

(58) Field of Classification Search
USPC ............................................. 435/161, 257.2
See application file for complete search history.

(56) References Cited

FOREIGN PATENT DOCUMENTS

| | | |
|---|---|---|
| JP | 2002-10779 | 1/2002 |
| JP | 2003-81996 | 3/2003 |
| JP | 2005-65695 | 3/2005 |
| JP | 2006-180748 | 7/2006 |
| JP | 2006-325518 | 12/2006 |
| JP | 2006-325577 | 12/2006 |
| JP | 2007-111590 | 5/2007 |
| JP | 2007-152217 | 6/2007 |
| JP | 2007-167782 | 7/2007 |
| JP | 2008-156388 | 7/2008 |

OTHER PUBLICATIONS

International Search Report dated Feb. 17, 2009 issued in corresponding PCT Application No. PCT/JP2009/050915.

*Primary Examiner* — Maryam Monshipouri
(74) *Attorney, Agent, or Firm* — Kenyon & Kenyon LLP

(57) ABSTRACT

To provide a method for producing an ethanol which facilitates the processing of a solid component as a residue generated upon processing, while improving the recovery rate of heat energy contained in leftover food. The method for recovering and producing ethanol and oil is a method for producing ethanol by saccharification, fermentation, and distillation of leftover food. In this method, a three-phase centrifuge for performing separation into three phases of an oil component, an aqueous solution component, and a solid component is used in a step of solid-liquid separation of any one of a saccharified liquid, a fermented liquid, and a distillation waste liquid.

13 Claims, 6 Drawing Sheets

METHOD FOR RECOVERING AND PRODUCING ETHANOL AND OIL

This application is a national stage application of International Application No. PCT/JP2009/050915, filed Jan. 22, 2009, which is incorporated by reference in its entirety.

TECHNICAL FIELD

The present invention relates to methods for recovering and producing ethanol and oil which involve saccharification, fermentation, and distillation of leftover food to thereby produce ethanol.

The term "leftover food" as used herein includes various kinds of wastes for food generated in the stage where human beings produce, process, cook, eat, and drink. For example, the leftover foods include garbage disposal from households, food-based industrial wastes from food factories, waste foods discarded in a distribution stage (waste sweets, out-of-date foodstuffs recovered from a convenience store or the like, and leftover waste food discarded from restaurants or the like), waste foodstuffs au food services, hospitals, and the like, fruits removed to increase a sugar content in the stage of production or adjustment for supply and demand.

Specifically, the invention is directed to a method for recovering and producing ethanol and oil from leftover food.

BACKGROUND ART

It is known that recycle systems can be configured to produce ethanol as liquid fuel by ethanol-fermentation of carbohydrate and five and six monosaccharide components existing in, for example, rice, bread, noodles, and the like among leftover foods, such as garbage.

The method involves recovering and saccharifying organic wastes containing a source of sugar, such as starch, to obtain monosaccharide, adding ethanol fermentation yeast thereto to consume all monosaccharide for several hours to about several months, and then distilling an ethanol fermented liquid to separate and refine ethanol. In order to obtain the ethanol with a purity of 99% or more, azeotropy or a dehydration membrane is used.

Various methods for producing ethanol from leftover food have been hitherto proposed.

For example, Japanese Unexamined Patent Publication No. 2007-111590(the following Patent Document 1) discloses a method including a step of crushing garbage to form crushed particles, a step of producing a saccharified liquid by adjustment of a concentration of starch of the crushed particles and by addition of a saccharifying enzyme, a step of carrying out alcohol fermentation by inoculation of bacteria of *Zymomonas mobilis* previously grown into the saccharified liquid to thereby produce a fermentation broth, and a step of recovering ethanol by distilling the fermentation broth. Thus, the method is disclosed which can produce ethanol from the garbage with high efficiency by achieving a conversion ratio to glucose exceeding 45%, and which can recover the ethanol with high efficiency using garbage as a raw material, while contributing to production of the ethanol for addition to gasoline in our country.

Japanese Unexamined Patent Publication No. 2005-65695 (the following Patent Document 2) discloses a method for producing ethanol by fermentation using a raw material containing starch. The method includes a pellet formation step of forming a pellet from the raw material, a saccharification step of obtaining a saccharified pellet by inoculation of green mold into the pellet, and a solid fermentation step of performing solid fermentation by adjusting the water content of a fermentation broth consisting of the saccharified pellet, yeast, and water to 30 to 60% by weight at the start of fermentation. Thus, the method and system for producing ethanol is disclosed which does not eject a waste liquid in the process of producing alcohol by developing a new method and system for producing alcohol using the solid fermentation method.

Japanese Unexamined Patent Publication No. 2006-325577 (the following Patent Document 3) discloses a system including an alcohol producing unit, and a waste liquid processing and utilizing unit. The system has the alcohol producing unit, a saccharification unit, a concentrator, a first fermentor, a distiller, and a dehydrator, and is designed to produce alcohol (alcohol for fuel) from a biomass raw material (garbage). In the saccharification unit, lactic acid is formed by microbes living in the garbage, which lessens pH of a saccharified liquid. In the concentrator, the saccharified liquid is concentrated so as to set the concentration of whole sugar of the concentrated saccharified liquid in a range of 100 g/l to 300 g/l, while setting the pH of the concentrated saccharified liquid to about 4.0 due to the condensation of the lactic acid. Thus, the system is disclosed which efficiently utilizes the garbage, and which can effectively produce the alcohol without necessity of disinfection, pH adjustment, and addition of a nutrient source to yeast even in use of the yeast belonging to *Saccharomyces cerevisiae* for producing liquors.

The related art methods for producing ethanol disclosed in the above Patent Documents 1 to 3, however, would clog pipes with oil components contained in the saccharified liquid, which leads to the problem of reduction in heat recovery rate of starch contained in garbage.

Further, the related art ethanol recycle utilizes sugar contained in organic wastes as a raw material for ethanol, and thus has the problem that all materials other than sugar are ejected as residues.

Patent Document 1

Japanese Unexamined Patent Publication No. 2007-111590

Patent Document 2

Japanese Unexamined Patent Publication No. 2006-325577

Patent Document 3

Japanese Unexamined Patent Publication No. 2006-325577

DISCLOSURE OF THE INVENTION

Problems to be Solved by the Invention

It is therefore an object of the present invention to solve the foregoing problems in the related art, and to provide a method for producing an ethanol which facilitates the processing of a solid component as a residue generated upon processing, while improving the recovery rate of heat energy contained in leftover food.

Means of Solving the Problems

As a result of an elaborate study for solving the above problems, the invention provides a method for producing ethanol in which a three-phase centrifuge for performing separation into three phases of an oil component, an aqueous solution component, and a solid component is used in a step of solid-liquid separation of any one of a saccharified liquid, a fermented liquid, and a distillation waste liquid. This method facilitates the processing of the solid component as a residue generated upon processing, while improving the recovery rate of heat energy contained in leftover food. The summary of the invention is as follows, as described in the accompanying claims.

(1) The method for recovering and producing ethanol and oil according to the invention is a method for recovering and producing ethanol and oil by saccharification, fermentation, and distillation of leftover food. In this method, a three-phase centrifuge for performing separation into three phases of an oil component, an aqueous solution component, and a solid component is used in a step of solid-liquid separation of any one of a saccharified liquid, a fermented liquid, and a distillation waste liquid.

(2) In the method for recovering and producing ethanol and oil according to Item (1), the oil component, and the solid component are separated and recovered from the aqueous solution component by three-phase separation, and a liquid component is sent to a fermentor.

(3) In the method for recovering and producing ethanol and oil according to Item (1) or (2), the leftover food to which waste oil solidified in the form of gelatin or absorbed in a newspaper is added as a raw material, and is then held and stirred for 12 hours or more at a temperature of 60° C. or more in a saccharifier, whereby the waste oil is recovered in the saccharified liquid.

(4) In the method for recovering and producing ethanol and oil according to any one of Items (1) to (3), lipase is added to the saccharifier as an enzyme to decompose the oil component remaining in solid matter, so that an amount of oil recovered by the three-phase separation is increased.

(5) In the method for recovering and producing ethanol and oil according to any one of Items (1) to (4), solid matter contained in the aqueous solution not separated in the solid-liquid separation step is removed using a screen having a mesh size of 0.1 mm to 10 mm.

(6) In the method for recovering and producing ethanol and oil according to any one of Items (1) to (5), foreign substances, such as plastics, paper, bags, disposable chopsticks, metal, or crustaceans, are separated using a filter type press, a vibrating screen, a punching metal, and a mesh before the solid-liquid separation step.

(7) In the method for recovering and producing ethanol and oil according to any one of Items (1) to (6), a concentration of the saccharified liquid containing a plurality of kinds of sugar, salt, and a SS component (suspended solid matter component) is measured by a Brix meter (refractometer), so that the concentration is controlled in a predetermined range.

(8) In the method for recovering and producing ethanol and oil according to any one of Items (1) to (7), a residue separated as the solid component in the solid-liquid separation step or the like is processed in a waste disposal apparatus for burning or melting wastes other than the leftover food, and steam obtained by recovering waste heat generated upon the process is used for a concentrating step and a distillation step of the leftover food.

(9) In the method for recovering and producing ethanol and oil according to any one of Items (1) to (8), the water of the residue separated as the solid component in the solid-liquid separation step or the like is dried and processed in a dryer using hot-air through-flow drying and aerobic fermentation heat, and then the residue is burned or melted in the waste disposal apparatus.

(10) In the method for recovering and producing ethanol and oil according to any one of Items (1) to (9), the residue separated as the solid component in the solid-liquid separation step or the like is subjected to anaerobic fermentation, and inflammable gas recovered is used as a heat source for burning or melting disposed in the waste disposal apparatus, or as a heating steam source in an ethanol plant.

(11) In the method for recovering and producing ethanol and oil according to any one of Items (1) to (10), an aqueous solution separated from ethanol in the distillation step is re-used as water for addition to be used in the saccharification step, and the remaining aqueous solution is sprayed in the burning or melting step of the waste disposal apparatus.

(12) In the method for recovering and producing ethanol and oil according to any one of Items (1) to (11), the oil component obtained by separation at the three-phase centrifuge is reused as a recycled oil fuel after being processed by an oil-water separation step, a filtering step, or both steps.

(13) In the method for recovering and producing ethanol and oil according to any one of Items (1) to (12), the recycled oil fuel is used as fuel for an adjacent waste disposal apparatus for burning or melting wastes to thereby save fossil fuel for use in the waste disposal apparatus.

(14) In the method for recovering and producing ethanol and oil according to any one of Items (1) to (12), the oil component obtained by separation at the three-phase centrifuge is used as a raw material for a biodiesel fuel by an ester exchange reaction, a subcritical treatment, a heat treatment, or the like.

(15) In the method for recovering and producing ethanol and oil according to any one of Items (1) to (14), a free fatty acid mixed in the oil component reacts with alcohol by addition of a concentrated sulfuric acid as a catalyst to be esterized, or reacts with alcohol using an ion exchange resin as a catalyst to be esterized, so that a concentration of the free fatty acid is decreased.

(16) In the method for recovering and producing ethanol and oil according to Item (14) or (15), ethanol refined in the process is used as an alcohol to be used in the ester exchange and/or esterification step.

Effects

According to one aspect of the invention described in Item (1), the leftover food generally contains several % of oil, which would cause closing of a pipe, inhibition of fermentation, or the like. However, this can be avoided. The recovered oil component is a fuel with high calorific value which contains vegetable oil as a principal component, and thus can be effectively used as the fuel or the like.

According to another aspect of the invention described in Item (2), for example, the oil component, and the solid component are separated and recovered from the aqueous solution component by three-phase separation between the saccharification step and the fermentation step, and the liquid component is sent to the fermentor. Since a saccharification tank is generally held at a high temperature of 60° C. or more, the viscosity of oil becomes so low that the oil is easily recovered. Thus, the oil component will inhibit the ethanol fermentation in the fermentation step as the post-process, the factors for the inhibition can be eliminated in advance, and the closing of the pipe can be prevented in the following steps. In this way, the invention has more merits.

At standard home, after vegetable oil used in fritters or pan-fried food is absorbed into a newspaper or a kitchen paper, or is solidified in the form of gelatin by addition of a solidification material containing a fatty acid as a principal component, most of the vegetable oil is discarded as flammable waste. Recovering of the oil from the home is performed only at specific stations, and the recovery rate of the waste oil is low.

According to another aspect of the invention described in Item (3), the waste oil not recovered yet in the related art can be delivered in the same recovering route as that for the leftover food, which can greatly save labor of recovering and can drastically improve the recovery rate. The leftover food with the waste oil is then held and stirred for 12 hours or more at a temperature of 60° C. or more in the saccharifier. Most of the vegetable oil leached into the newspaper is dissolved into the saccharification liquid, or the oil solidified in the form of gelatin can be converted into a liquid at a temperature of about 60° C., so that the oil can be easily recovered in the following steps.

According to another aspect of the invention described in Item (4), the oil component attached to the solid matter and the oil component in the form of a solid can be decomposed by addition of lipase as an enzyme, which can further enhance the recovery rate of the oil.

According to another aspect of the invention described in Item (5), the solid matter not separated in the liquid separation step is removed by the screen having a mesh size of 0.1 mm to 10 mm, and thus does not cause inhibition of the operations in the post-processes, such as the concentrating step, the fermentation step, or the distillation step.

According to another aspect of the invention described in Item (6), foreign substances, such as plastics, paper, bags, disposable chopsticks, metal, or crustaceans, are separated using a filter type press, a vibrating screen, a punching metal, and a mesh before the solid-liquid separation step. In this way, the foreign substances which cannot be removed completely by a crushing separator can be separated.

According to another aspect of the invention described in Item (7), the concentration of the saccharified liquid containing a plurality of kinds of sugar, salt, and a SS component (suspended solid matter component) is measured and managed by the Brix meter (refractometer). Thus, the management of the concentration can be accurately performed by adjustment of a mixing ratio between these raw materials, or by changing of the concentrating degree in the case of providing the concentrating step of the saccharified liquid. Accordingly, the fermentation state can be continued stably.

According to another aspect of the invention described in Item (8), the residue separated as solid matter in the solid-liquid separation step, or by the screen, the dehydrator, or the like provided in each unit is processed in a waste disposal apparatus for burning or melting wastes other than the leftover food together with the wastes. Steam obtained by recovering waste heat generated upon the process can be used for the concentrating step and the distillation step of the leftover food. The electric power generation of the wastes uses the heat energy of the steam, and converts it into electricity. The efficiency of electric power generation is about at most 35%, which is low. Most of the heat energy is lost as condensed water when the steam vapor condenses to water. However, the heat level required in the concentrating step or distillation step of the invention is about 100° C. The liquid fuel which is easy to handle and preserve can be taken out by the use of the waste heat lost in the related art, which is very excellent in terms of energy efficiency.

Even when the residue is mechanically squeezed, for example, using the dehydrator, the residue has a water content of 70% or more. Thus, when the residue is burned and melted as it is, another external fuel is required and the rate of steam obtained by recovering the waste heat remains low.

According to another aspect of the invention described in Item (9), incorporation of the through-flow-drying using the low level waste heat at a temperature of 60° C. or more, and the aerobic drying using the fermentation heat of microbes contained in the leftover food (to which new bacteria may be added) can drastically reduce the water content without newly adding an external fuel thereto. Thus, new external fuel does not need to be used in the adjacent burning or melting apparatus, which can enhance the rate of steam obtained by recovering the waste heat.

According to another aspect of the invention described in Item (10), while the residue remains in the anaerobic state, the inflammable gas containing methane as a principal component can be recovered by the action of microbes contained in the leftover food (to which new bacteria may be apparently added). This technique activates the action of microbes by holding and stirring the solubilized raw material at a temperature of 35° C. or more in a concentration of solid matter of about 10% in a tank. The residue in the invention is already solubilized, and by addition of distilled waste water or the like, the fermentation can be carried out easily without adding new water and fuel. The recovered inflammable gas, such as methane, can be used as an alternative to external fuel in an adjacent burning or melting apparatus. Further, the use of an independent gas engine generator or gas turbine generator using the inflammable gas, or a superheated steam obtained from the waste heat of a steam generator can cover a part of the power or steam in the station.

According to another aspect of the invention described in Item (11), a part of the distillation waste liquid is re-used as water for addition to the saccharification step to thereby decrease the amount of waste liquid, which can further obtain heat (at 60° C.) required for the saccharification step. The waste liquid containing an organic component cannot be flown as the waste water without being processed as it is, but is sprayed toward a high-temperature part of the adjacent burning furnace or melting furnace, whereby the organic component can be burned and rendered harmless.

According to another aspect of the invention described in Item (12), the oil component obtained by separation at the three-phase centrifuge can be used as the recycled oil fuel by being processed in the oil-water separation step, the filtering step, or both steps.

According to another aspect of the invention described in Item (13), the recycled oil fuel is used as fuel for an adjacent waste disposal apparatus for burning or melting wastes to thereby save fossil fuel for use in the waste disposal apparatus. The waste heat generated due to the combustion by the burning process is recovered as steam. For example, the bleed steam taken at the time of electric power generation using the steam turbine can be used for the concentrating step and the distillation step of the leftover food.

According to another aspect of the invention described in Item (14), it has found that the oil component obtained by separation at the three-phase centrifuge is an oil containing vegetable oil as a principal component, and can be used as one corresponding to a diesel oil by the following process. (a) One method is an alkali process method which involves adding alcohol to the oil as a raw material obtained in the invention using KOH or NaOH as a catalyst, whereby the oil can be decomposed into a fatty acid and a glycerin (ester exchange reaction). The thus-obtained fatty acid can be used as the diesel oil after removing the glycerin and the alkali catalyst. (b) Another method is a subcritical method. The subcritical method involves bringing the oil as a raw material to a subcritical state to cause the oil to be decomposed into a glycerin and a fatty acid. This method enables the decomposition without a special pre-process even when the raw material is relatively dirty.

According to another aspect of the invention described in Item (15), the oil component obtained by the invention has a free fatty acid mixed therein, and would form a soap via an alkali catalyst as it is. Thus, it is necessary to previously remove the free fatty acid before the ester exchange reaction. The free fatty acid can be esterized by being reacted with an alcohol using a concentrated sulfuric acid as a catalyst. Thereafter, as described in Item (14), the thus-obtained oil component is reacted with the alcohol via the alkali catalyst, so that the diesel oil can be produced without producing a soap component. Similarly, the free fatty acid can be esterized using an ion exchange resin. The combination of the ion exchange resin can also promote the ester exchange in terms of technique.

Methanol is generally known as the alcohol used in the esterification reaction and/or ester exchange reaction. Methanol is ordinarily synthesized from petroleum. Thus, methanol can be technically made of a biomass (note that the biomass is gasified and then methanol is synthesized from the synthesized gas via a catalyst), which is highly difficult under a high pressure in terms of technique. According to another aspect of the invention described in Item (16), the ethanol produced from the leftover food can be used as a sub-raw material for refining a biodiesel fuel, so that all diesel oil can be produced using raw materials derived from the biomass.

The above-mentioned reaction generally has its efficiency reduced due to the intrusion of water, but can use a dehydrated ethanol which is dehydrated (by membrane separation, PSA, or azeotropic distillation) after the distillation.

The invention can provide the method for recovering and producing ethanol and oil in which the three-phase centrifuge for performing separation into three phases of an oil component, an aqueous solution component, and a solid component is used in the solid-liquid separation step of any one of the saccharified liquid, the fermented liquid, and the distillation waste liquid. Thus, the method facilitates the process of the solid component as the residue generated upon the process, while improving the recovery rate of heat energy contained in leftover food.

The steam recovered from the burning (melting) furnace can be effectively used to reduce the manufacturing cost of ethanol.

Further, the burned heat from the residue can be used for manufacturing of ethanol; and can also be used as a recycled oil fuel. The invention significantly produces industrially useful effects.

Figure 1:
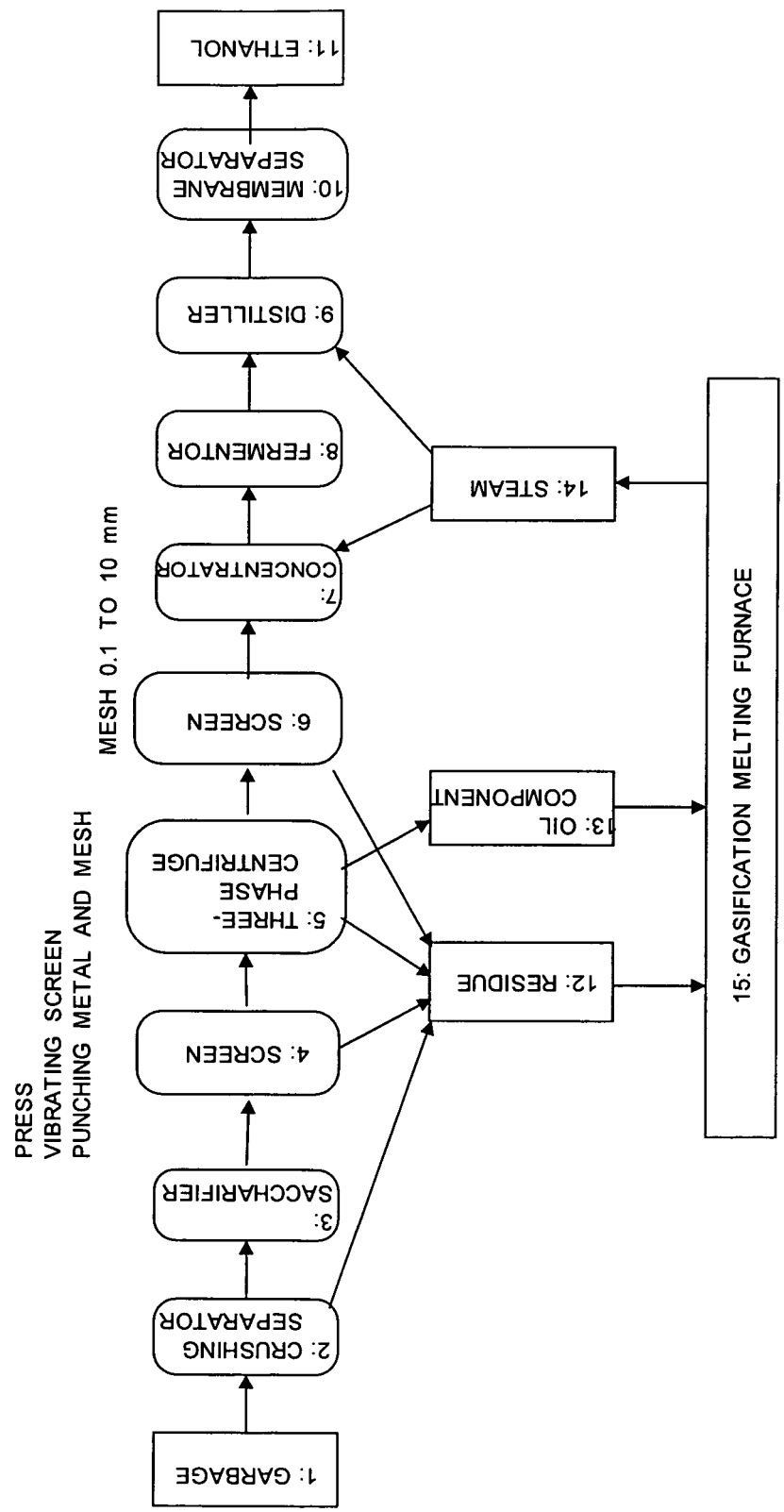
FIG. 1 is a diagram exemplifying a method for recovering and producing ethanol and oil according to a first embodiment of the invention.

DESCRIPTION OF REFERENCE NUMERALS 1 garbage
2 crushing separator
3 saccharifier
4 screen
5 three-phase centrifuge
6 screen
7 concentrator
8 fermentor
9 distiller
10 membrane separator
11 ethanol
12 residue(solid component)
13 oil component
14 steam
15 gasification melting furnace
16 waste liquid
17 oil recycling process
18 fuel production process

BEST MODE FOR CARRYING OUT THE INVENTION

Best modes and examples for carrying out the invention will be described in detail below using FIGS. 1 to 6.

FIGS. 1 to 4 illustrates a garbage 1, a crushing separator 2, a saccharifier 3, a screen 4, a three-phase centrifuge 5, a screen 6, a concentrator 7, a fermentor 8, a distiller 9, a membrane separator 10, ethanol 11, a residue (solid component) 12, an oil component 13, steam 14, a gasification melting furnace 15, a waste liquid 16, an oil recycling process 17, and a fuel production process 18. The same elements are designated by the same reference characters, so that a repeated description thereof will be omitted.

First Embodiment

FIG. 1 is a diagram exemplifying a method for producing ethanol according to a first embodiment of the invention.

First, a sample of the garbage 1 is crushed using the crushing separator 2. After removing a solid component as a residue 12 therefrom, the crushed garbage is kept in the saccharifier 3 at a temperature of about 60° C. with enzyme, such as glucoamylase, added thereto, so that starch is converted into glucose which is soluble in water.

Then, foreign substances, such as plastics, paper, bags, disposable chopsticks, metal, or crustaceans, are separated using a filter type press, a vibrating screen, a punching metal, and a mesh in the screen 4, and are removed as the residue 12. Then, the sample of the garbage is separated into three phases, namely, an oil component, an aqueous solution component, and a solid component, by the three-phase centrifuge 5 with the solid component removed therefrom as the residue 12. The separated oil component 13 can be used as fuel for the gasification melting furnace 15. The separated aqueous solution component does not contain any oil component, which can prevent reduction in thermal efficiency of an ethanol producing apparatus without being considered about clogging of a pipe for the solution due to the attachment of the oil component to the pipe. A temperature of a saccharified liquid directly after the saccharifier 3 is equal to or more than 28° C., which can enhance the flexibility of the oil component to thereby facilitate the separation and recovering of the oil component.

Then, in the screen 6, solid matter not separated in the solid-liquid separation step is removed using a screen having a mesh (aperture) size of 0.1 mm to 10 mm as the residue 12. The sample is heated to about 160° C. by the concentrator 7 to form a glucose aqueous solution having a concentration of about 15 WT %. Then, in the fermentor 8, yeast can break down glucose to form ethanol having a concentration of about 7.5 WT %.

The invention can improve the energy efficiency by using the bleed steam 14 with an intermediate-low temperature of about 200° C. which is used in an electric power apparatus of the gasification melting furnace 15, regardless of the presence or absence of the concentrator 7, and a heat source.

For example, during the period of time from the saccharification step to the fermentation step, the oil component and the solid component are separated and recovered from the aqueous solution component by three-phase separation, and a liquid component is fed to the fermentor. Since a saccharification tank is generally held at a high temperature of 60° C. or more, the viscosity of oil becomes so low that the oil is easily recovered. The factors for the inhibition of fermentation in the post-process can be eliminated in advance, and the closing of the pipe can be prevented in the following steps. In this way, the invention has more merits.

The ethanol fermentation can be utilized by addition of sugar sources, such as old rice or woody saccharified material. This can ensure the source of nitrogen at a low cost which occupies half a cost of raw materials in the general ethanol fermentation. For example, the leftover food to which waste oil solidified in the form of gelatin or absorbed in a newspaper is added is used as the raw material, and then held and stirred for 12 hours or more at a temperature of 60° C. or more in the saccharifier. The waste oil which was not able to be recovered in the related art can be delivered in the same recovering route as that for the leftover food, which can greatly save labor of recovering and can drastically improve the recovery rate. Further, since the leftover food is then held and stirred for 12 hours or more at a temperature of 60° C. or more in the saccharifier, most of vegetable oil dissolved in the newspaper leaches into a saccharified liquid, or oil solidified in the form of gelatin can be converted into a liquid at a temperature of about 60° C. The oil can be easily recovered in the following steps.

Since the oil attached to solid matter can be decomposed by addition of lipase thereto, the recovery rate of oil can be further improved.

The water of the residue separated as the solid component in the solid-liquid separation step or the like is dried and processed in a dryer using hot-air through-flow drying and aerobic fermentation heat, and then the residue is burned or melted in the waste disposal apparatus. The incorporation of the through-flow drying using low-level waste heat at 60° C. or more, or the aerobic drying using the fermentation heat of microbes contained in the leftover food (to which new bacteria may be apparently added) can drastically reduce the water without newly adding an external fuel thereto. Thus, it is not necessary to provide a new external fuel in an adjacent burning or melting apparatus, which can enhance the rate of steam obtained by recovering the waste heat.

The residue separated as the solid component in the solid-liquid separation step or the like is subjected to anaerobic fermentation, and inflammable gas recovered is used as a heat source for burning or melting in the waste disposal apparatus, or as a heating steam source in an ethanol plant. While the residue remains in the anaerobic state, the inflammable gas containing methane as a principal component can be recovered by the action of microbes contained in the leftover food (to which new bacteria may be apparently added). This technique activates the action of microbes by holding and stirring the solubilized raw material at a temperature of 35° C. or more in a concentration of the solid component of about 10% in a tank. The residue in the invention is already solubilized, and by addition of distilled waste water or the like, the fermentation can be carried out easily without adding new water and fuel. The recovered inflammable gas, such as methane, can be used as an alternative to external fuel in an adjacent burning or melting apparatus. Further, the use of an independent gas engine generator using the inflammable gas, or a steam generator or the like can cover a part of the power or steam in the station.

The aqueous solution separated from ethanol concentrated and recovered in the distillation step is re-used as water for addition to be used in the saccharification step, and is sprayed in the remaining burning or melting step of the waste disposal apparatus, which can lessen the amount of waste solution, and can obtain heat (of 60° C.) required for the saccharification step. The waste solution contains organic components, and cannot be thrown as waste water as it is. However, by spraying the waste solution to a high-temperature part of an adjacent burning furnace or melting furnace, the organic components can be rendered harmless by burning.

In the ethanol fermentation, in order to effectively ferment ethanol from a saccharified liquid formed from the leftover food, a Brix meter (refractometer) not shown is disposed on an outlet side of the concentrator 7 to measure the concentration of the saccharified liquid containing various types of sugar, salt, and SS components (suspension solid matter component). In order to set the concentration within a prescribed range, a ratio of mixing between the raw materials is changed or the degree of concentrating of the saccharified liquid is adjusted. Thus, the concentration of the saccharified liquid is managed so that the effective fermentation can be maintained.

After converting the sugar into ethanol by the ethanol fermentation, the ethanol is separated from the ethanol fermented liquid by the distiller 9, and then the dehydrated ethanol with a purity of about 99.5% or more can be refined by the membrane separator 10.

By use of garbage, organic wastes contain not only a sugar source, but also a nitrogen source and nutrition, such as vitamin or mineral. It is not necessary to add new nutrition upon the ethanol fermentation. The produced ethanol can be used as an antiseptic solution, a liquid fuel, and a fuel for vehicles.

Instead of the gasification melting furnace 15, a burning furnace can be used. The burning furnace or melting furnace to be used can be the existing furnace.

Second Embodiment

Figure 2:
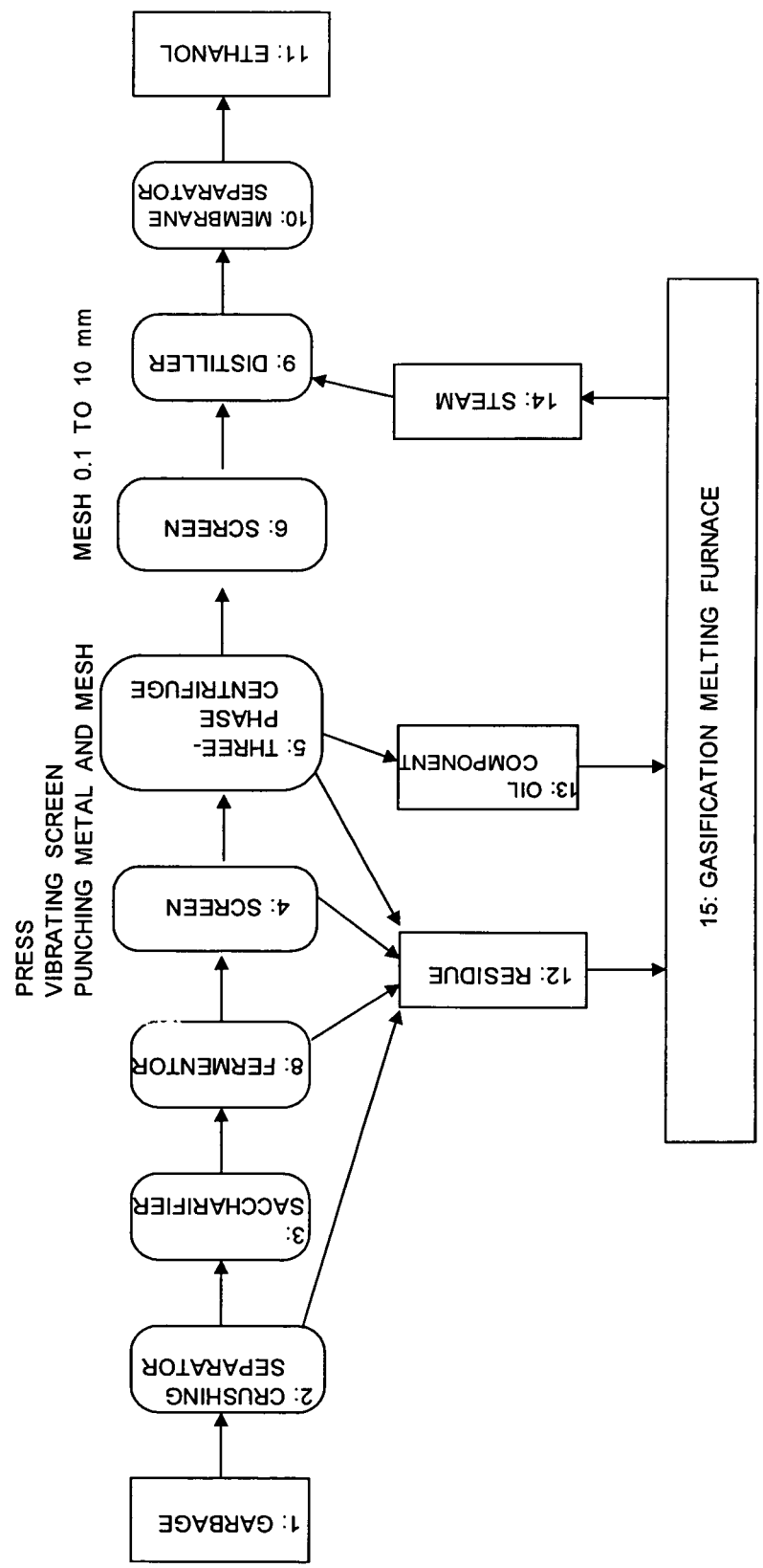
FIG. 2 is a diagram exemplifying a method for recovering and producing ethanol and oil according to a second embodiment of the invention.

FIG. 2 is a diagram exemplifying a method for producing ethanol according to a second embodiment of the invention.

In the second preferred embodiment, the screen 4, the three-phase centrifuge 5, and the screen 6 of the first embodiment are set between the fermentor 8 and the distiller 9. A part of the solid component is supplied to the fermentor 8, which can improve the efficiency of fermentation. Since the temperature of the saccharified liquid directly after the saccharifier 3 is equal to or more than 28° C. or more, the flexibility of the oil component can be enhanced, thus facilitating the separation and recovering of the oil.

The features of the screen 4, the screen 6, and the Brix meter (refractometer) are the same as those of the first embodiment.

Third Embodiment

Figure 3:
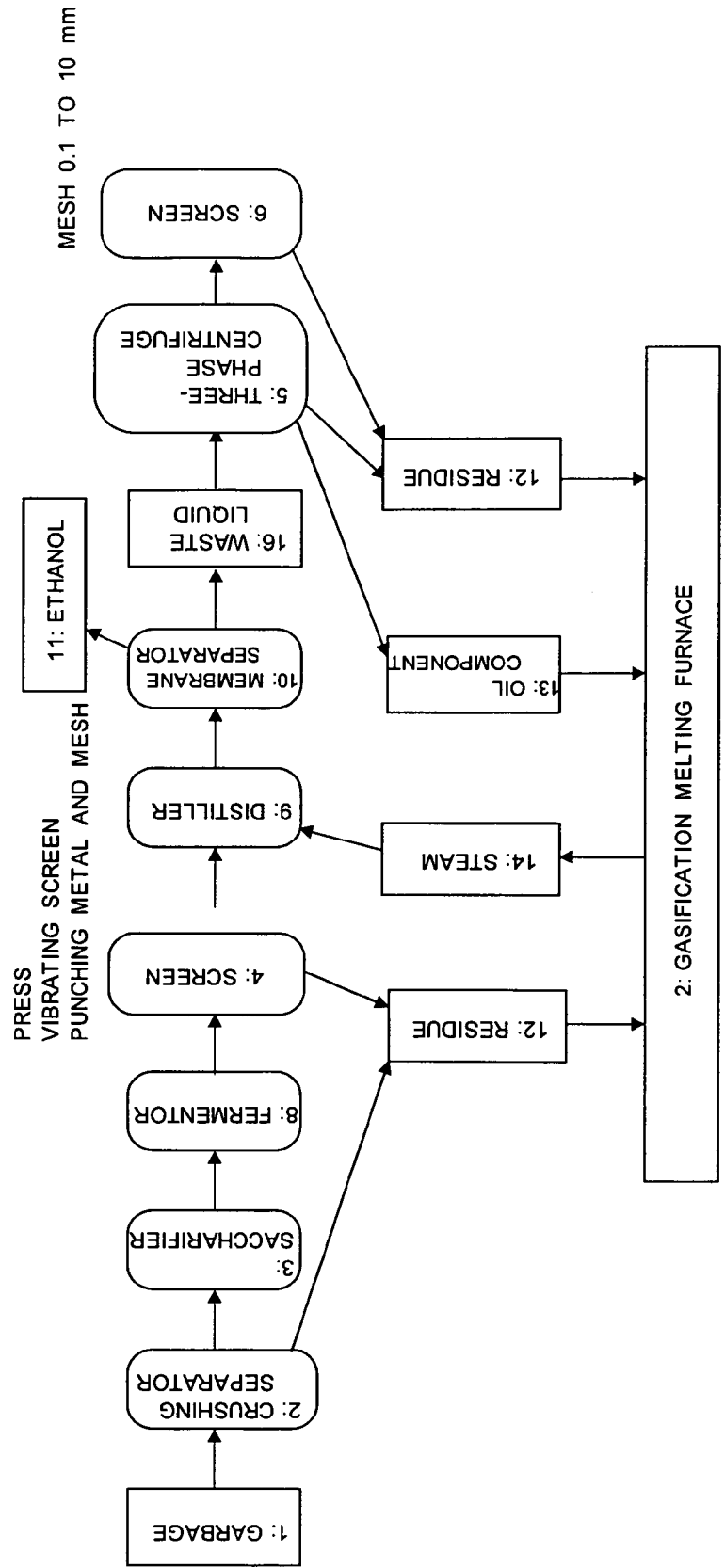
FIG. 3 is a diagram exemplifying a method for recovering and producing ethanol and oil according to a third embodiment of the invention.

FIG. 3 is a diagram exemplifying a method for producing ethanol according to a third embodiment of the invention.

In the third embodiment, the screen 4 of the first embodiment is disposed between the fermentor 8 and the distiller 9, and the three-phase centrifuge 5 and the screen 6 are disposed after the membrane separator 10, whereby a part of the solid component is supplied to the fermentor 8, the distiller 9, and the membrane separator 10 to enable improvement of the ethanol formation efficiency. Since the temperature of the saccharified liquid directly after the distiller 9 is equal to or more than 40° C. or more, the flexibility of the oil component can be enhanced, thus facilitating the separation and recovery of the oil.

The features of the screen 4, the screen 6, and the Brix meter (refractometer) are the same as those of the first embodiment.

EXAMPLES

Figure 4:
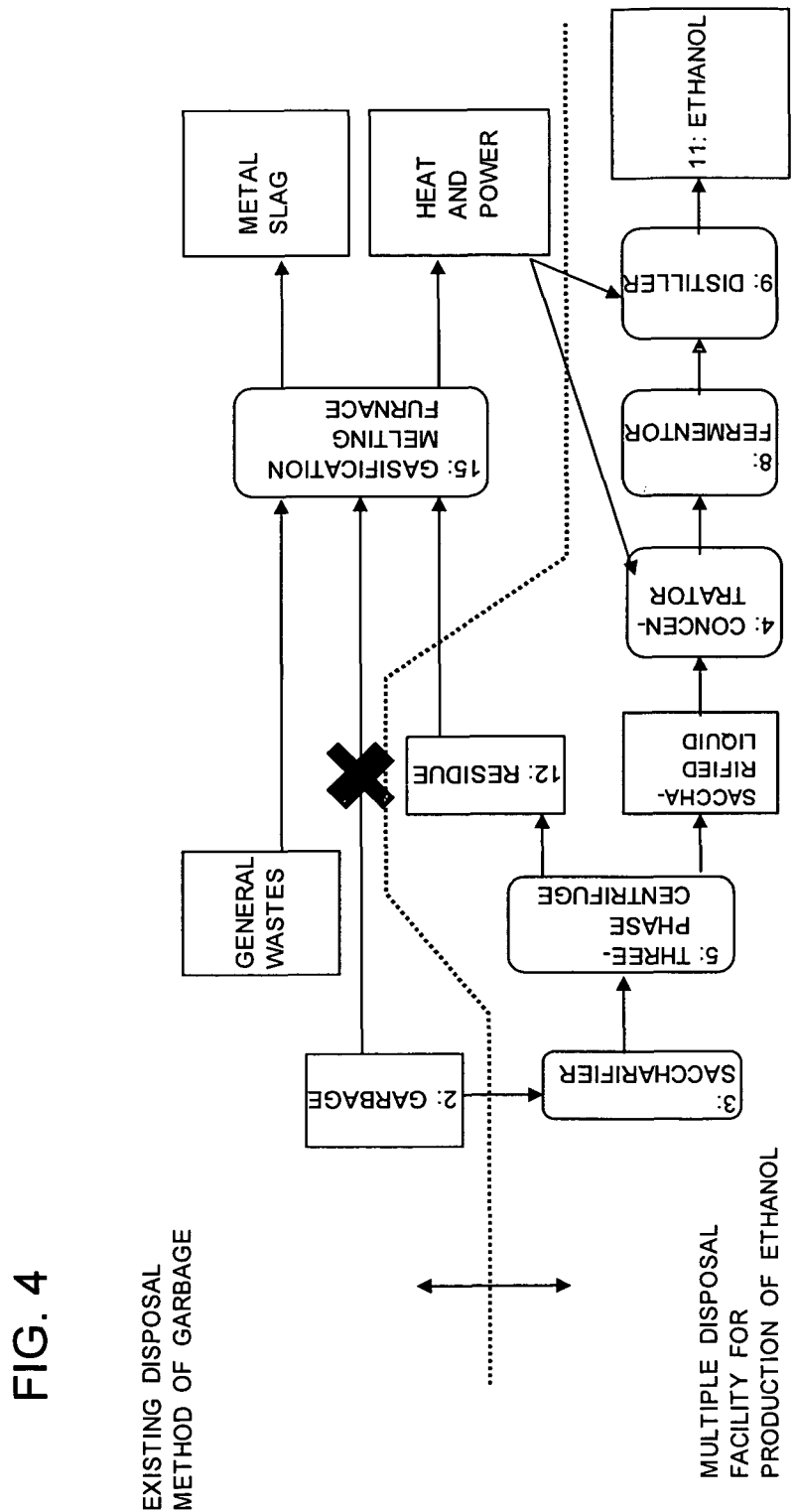
FIG. 4 is a diagram showing an example of the method for recovering and producing ethanol and oil in the invention.
Figure 5:
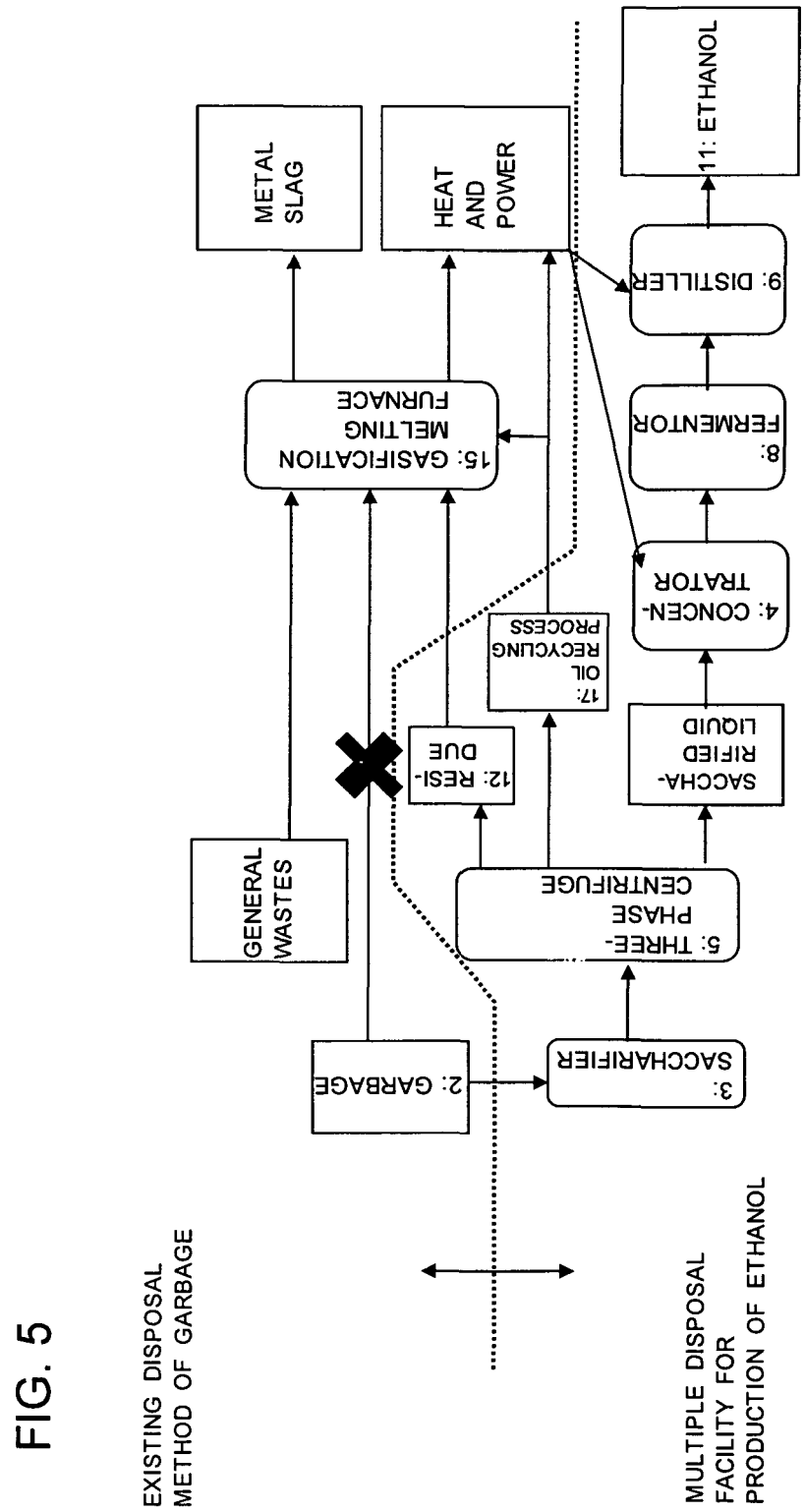
FIG. 5 is a diagram showing another example of the method for recovering and producing ethanol and oil in the invention.
Figure 6:
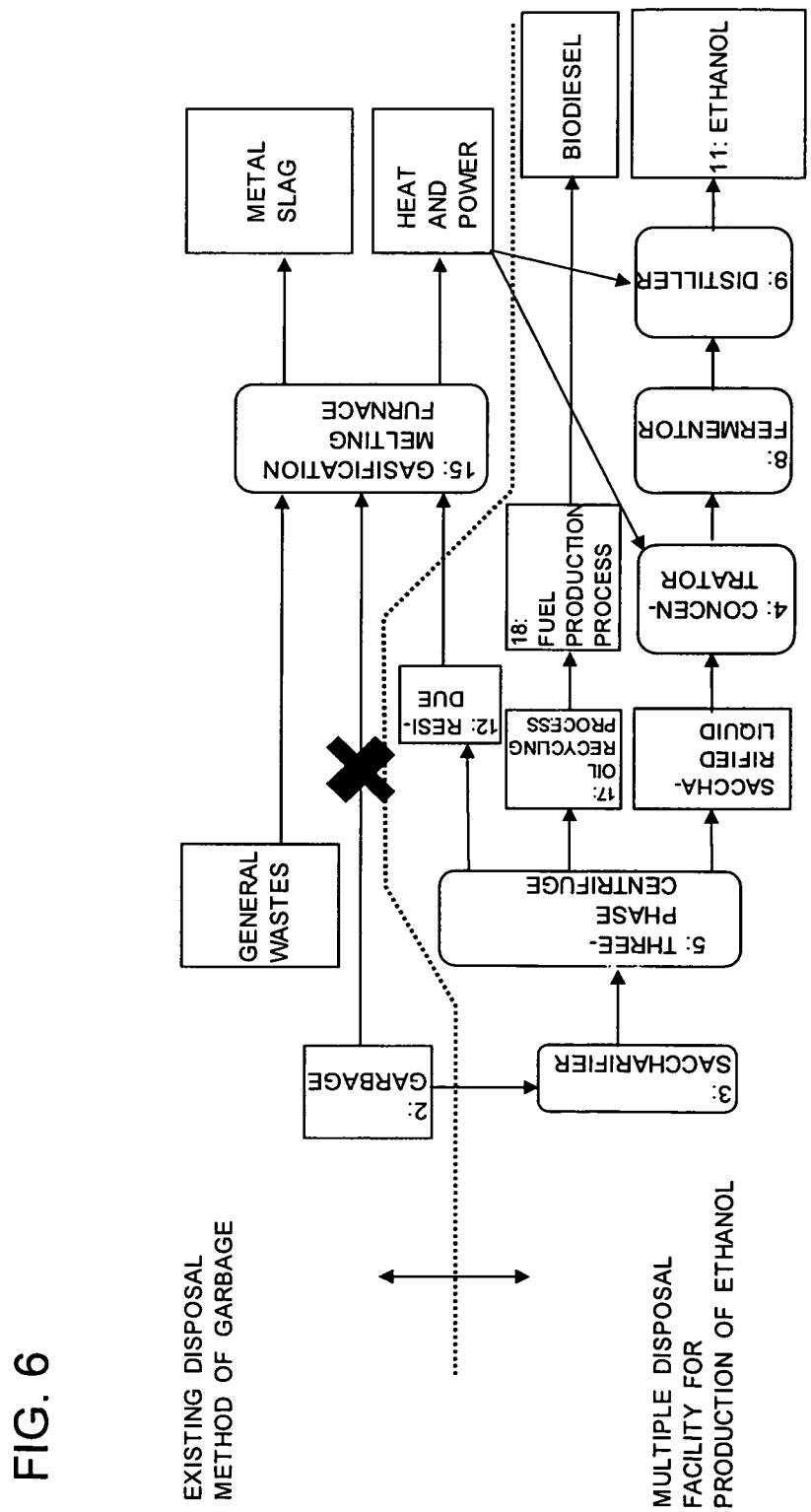
FIG. 6 is a diagram showing a further example of the method for recovering and producing ethanol and oil in the invention.

Tests were performed in which the method for producing ethanol according to the invention was applied to an ethanol production apparatus adjacent to the gasification melting furnace shown in FIGS. 4 to 6.

It was confirmed that the thermal efficiency was able to be improved by using the bleed steam at an intermediate-low temperature of about 200° C. generated in the gasification melting furnace 15 as heat sources for the concentrator 7 and the distiller 9 of the ethanol production apparatus, while processing the residue 12 generated from the ethanol production apparatus by use of the gasification melting furnace 15.

When producing 400 liters/day of ethanol using 10 t/day of garbage, 90% of heat energy contained in the garbage was able to be recovered as the ethanol. Thus, the effect of the invention was able to be confirmed.

FIGS. 5 and 6 show examples for recycling an oil component separated using the three-phase centrifuge.

As shown in FIGS. 5 and 6, it has been found that the oil component obtained by separation at the three-phase centrifuge 5 can be used as the recycled oil fuel by being processed by the oil recycling process 17 including an oil-water separation step, a filtering step, or both steps.

It has been also found that the recycled oil fuel is used as fuel for the adjacent waste disposal apparatus for burning or melting wastes to thereby save fossil fuel for use in the waste disposal apparatus. Alternatively, it has been found that waste heat generated by burning the recycled oil is used for electric power generation, and that a bleed steam at the time of the power generation can be used in the concentrating step and the distiller step of the leftover food.

Further, it has been found that the oil component obtained by separation at the three-phase centrifuge 5 can be used as a raw material for a biodiesel fuel containing a fatty acid methyl ester, by the fuel production process 18 including an ester exchange reaction, a subcritical treatment, and the like.

INDUSTRIAL APPLICABILITY

According to the invention, the residue generated in the ethanol production apparatus can be easily processed by the gasification melting furnace, and the bleed steam for use in the electric power generation of the gasification melting furnace is used as a heat source necessary for the ethanol production apparatus, which can enhance the thermal efficiency. The invention is very effective when the gasification melting furnace is disposed in the vicinity of the ethanol production apparatus. The invention is expected to have high hopes for the future of upcoming projects of the ethanol production apparatus.

The invention claimed is:

1. A method for recovering and producing ethanol and/or oil, comprising the steps of:
    crushing leftover food using a crushing separator and removing a first solid component, wherein the leftover food includes any of garbage disposal from households, waste foods discarded in a distribution stage, and waste foodstuffs from food services or hospitals;
    saccharifying the crushed leftover food in a saccharifier such that a saccharified liquid directly after the saccharifier is at a temperature of 28° C. or more by addition of an enzyme into the saccharifier to convert starch into glucose which is soluble in water;
    separating and removing substances including one or more of plastics, paper, bags, disposable chopsticks, metal, and crustaceans using a screen as a second solid component; and
    separating the saccharified leftover food into an oil component, an aqueous solution component, and a third solid component by a three-phase centrifuge, wherein the oil component is recovered from the aqueous solution component, and the aqueous solution component is fed to a fermentor to produce ethanol, thereby recovering and producing ethanol and/or oil.

2. The method for recovering and producing ethanol and/or oil according to claim 1, wherein the leftover food contains waste oil solidified in the form of gelatin or absorbed in a newspaper, and wherein the leftover food is held and stirred for 12 hours or more at a temperature of 60° C. or more in the saccharifier, and the waste oil is recovered in the saccharified liquid.

3. The method for recovering and producing ethanol and/or oil according to claim 1, further comprising adding a lipase into the saccharifier to decompose oil remaining in a solid form, so that an amount of oil recovered by the three-phase separation is increased.

4. The method for recovering and producing ethanol and/or oil according to claim 1, further comprising removing remaining solid matter contained in the aqueous solution not separated in the solid-liquid separation step is removed using a screen having a mesh size of 0.1 mm to 10 mm as a fourth solid component.

5. The method for recovering and producing ethanol and/or oil according to claim 1, wherein a concentration of the saccharified liquid containing a plurality of sugars, salt, and a suspended solid component is measured using a Brix meter or a refractometer, and wherein the concentration of the saccharified liquid is controlled in a predetermined range.

6. The method for recovering and producing ethanol and/or oil according to claim 4, further comprising processing the first, second, third, and/or fourth solid component in a waste disposal apparatus for burning or melting wastes other than the leftover food, and using steam obtained by recovering waste heat generated by burning or melting for a concentrating step and a distillation step.

7. The method for recovering and producing ethanol and/or oil according to claim 6, further comprising drying the first, second, third, and/or fourth solid component in a dryer using hot-air through-flow drying and aerobic fermentation heat, and then burning or melting the residue in the waste disposal apparatus.

8. The method for recovering and producing ethanol and/or oil according to claim 6, further comprising subjecting the first, second, third, and/or fourth solid component to anaerobic fermentation, and recovering and using inflammable gas as a heat source for burning or melting in the waste disposal apparatus, or as a heating steam source in an ethanol plant.

9. The method for recovering and producing ethanol and/or oil according to claim 6, further comprising using an aqueous solution separated from ethanol in the distillation step for addition in the saccharification step, and spraying the remaining aqueous solution in the burning or melting step of the waste disposal apparatus.

10. The method for recovering and producing ethanol and/or oil according to claim 1, further comprising processing the oil component obtained by the three-phase centrifuge in one or both of an oil-water separation step and a filtering step to produce a recycled oil fuel.

11. The method for recovering and producing ethanol and/or oil according to claim 10, further comprising using the recycled oil fuel in an adjacent waste disposal apparatus for burning or melting wastes to save fossil fuel.

12. The method for recovering and producing ethanol and/or oil according to claim 1, further comprising using the oil component obtained by the three-phase centrifuge as a raw material for producing a biodiesel fuel by an ester exchange reaction, a subcritical treatment, or a heat treatment.

13. The method for recovering and producing ethanol and/or oil according to claim 1, further comprising fermenting a saccharified liquid containing the aqueous solution component in a fermentor to produce ethanol.

* * * * *

UNITED STATES PATENT AND TRADEMARK OFFICE
CERTIFICATE OF CORRECTION

PATENT NO.        : 8,722,372 B2  
APPLICATION NO. : 13/138223  
DATED             : May 13, 2014  
INVENTOR(S)       : Kiuchi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Signed and Sealed this

Twenty-ninth Day of September, 2015

Michelle K. Lee
*Director of the United States Patent and Trademark Office*